United States Patent [19]

Hsia

[11] 4,374,857

[45] Feb. 22, 1983

[54] METHOD OF INHIBITING L-TRYPTOPHAN TO SERUM ALBUMIN BINDING

[75] Inventor: Jen C. Hsia, Concord, Canada

[73] Assignee: Her Majesty the Queen in right of Canada, as represented by the Minister of National Defence, Ottawa, Canada

[21] Appl. No.: 342,236

[22] Filed: Jan. 25, 1982

[51] Int. Cl.$^3$ .............................................. A61K 31/19
[52] U.S. Cl. ................................................... 424/317
[58] Field of Search ......................................... 424/317

[56] References Cited
PUBLICATIONS

Chem. Abst., vol. 85, (1976)–16643c.

Primary Examiner—Stanley J. Friedman
Attorney, Agent, or Firm—Cushman, Darby & Cushman

[57] ABSTRACT

The invention disclosed is a method of inhibiting L-tryptophan to serum albumin binding in a biological fluid containing L-tryptophan and serum albumin, comprising adding to the fluid cis-parinaric acid in a molar ratio to serum album of about 0.5:1 to 4.0:1.

11 Claims, 4 Drawing Figures

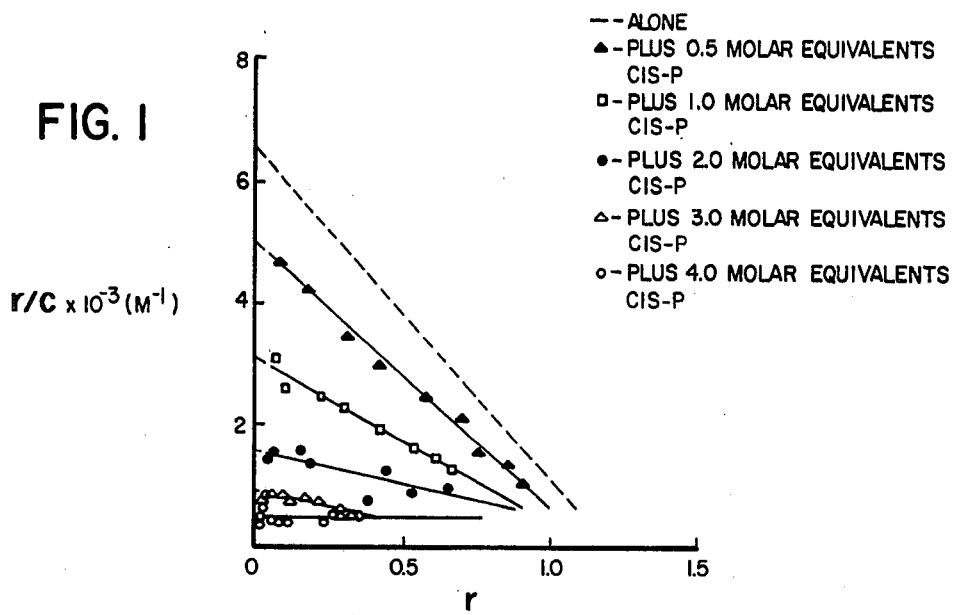

SCATCHARD PLOT OF $^{14}$C-L-TRP BINDING TO $1 \times 10^{-4}$M HUMAN SERUM ALBUMIN ALONE AND IN THE PRESENCE OF VARIOUS MOLAR EQUIVALENTS OF CIS-PARINARATE IN RINGER'S BUFFER, pH 7.4 AT 37°C, WHEREIN r IS MOLES OF $^{14}$C-L-TRP BOUND/MOLE OF ALBUMIN AND C IS FREE $^{14}$C-L-TRP CONCENTRATION.

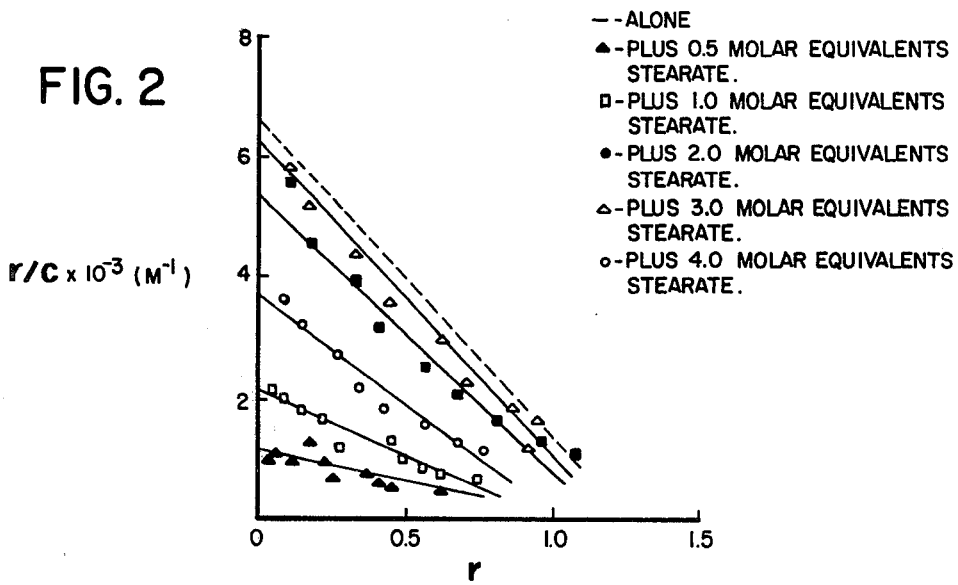

SCATCHARD PLOT OF $^{14}$C-L-TRP BINDING TO $1 \times 10^{-4}$M HUMAN SERUM ALBUMIN ALONE AND IN THE PRESENCE OF VARIOUS MOLAR EQUIVALENTS OF STEARATE IN RINGER'S BUFFER, pH 7.4 AT 37°C, WHEREIN r IS MOLES OF $^{14}$C-L-TRP BOUND/MOLE OF ALBUMIN AND C IS FREE $^{14}$C-L-TRP CONCENTRATION.

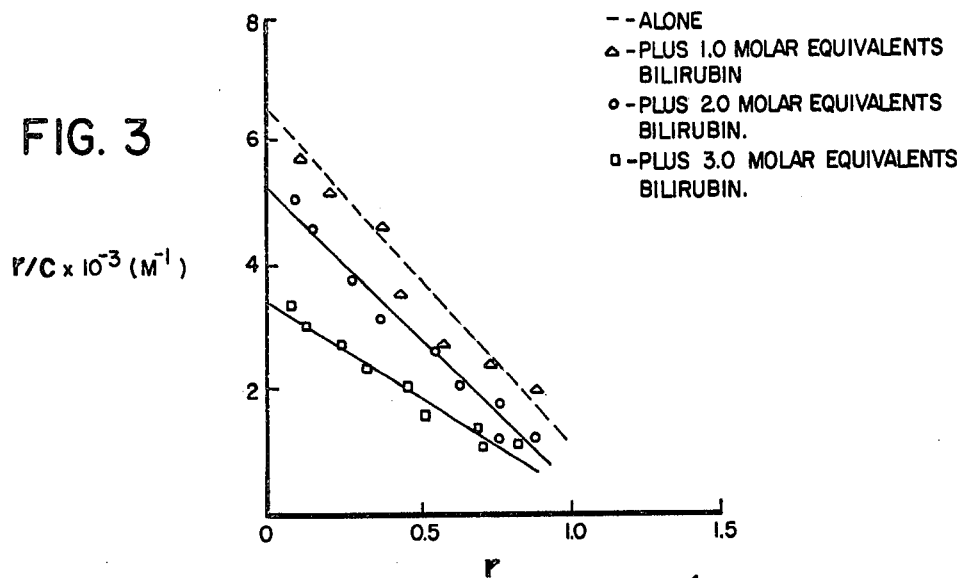

SCATCHARD PLOT OF $^{14}$C-L-TRP BINDING TO $1 \times 10^{-4}$M HUMAN SERUM ALBUMIN ALONE AND IN THE PRESENCE OF VARIOUS MOLAR EQUIVALENTS OF BILIRUBIN IN RINGER'S BUFFER, pH 7.4 AT 37°C, WHEREIN r IS MOLES OF $^{14}$C-L-TRP BOUND/MOLE OF ALBUMIN AND C IS FREE $^{14}$C-L-TRP CONCENTRATION.

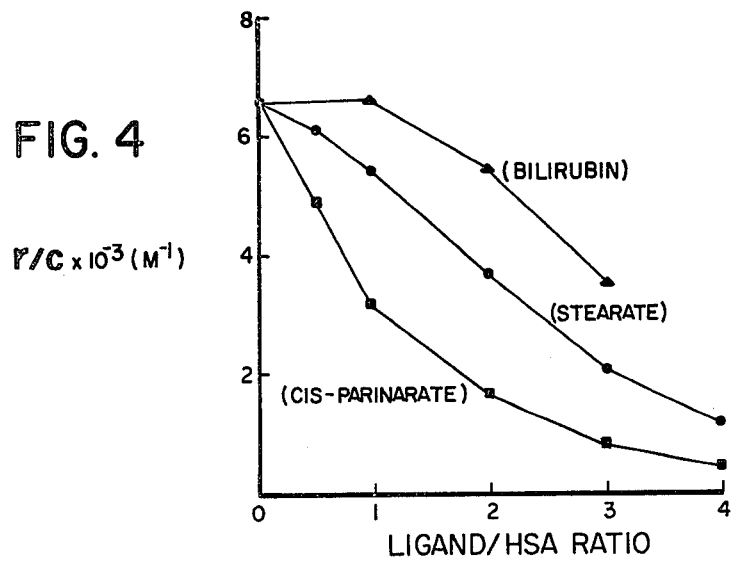

EFFECTS OF LIGANDS BILIRUBIN, STEARATE AND CIS-PARINARATE ON THE r/C VALUES OF $^{14}$C-L-TRP BOUND TO HUMAN SERUM ALBUMIN.

METHOD OF INHIBITING L-TRYPTOPHAN TO SERUM ALBUMIN BINDING

BACKGROUND OF THE INVENTION

This invention relates to the binding of L-tryptophan to human serum albumin in a biological fluid, and in particular to a method of inhibiting this binding.

Serum albumin is the most abundant plasma protein. It's major functions are regulation of osmotic pressure and transport of a wide variety of drugs (usually carrying a negative charge), and endogenous substances such as bilirubin, fatty acids and L-tryptophan (L-TRP). It is clear that although albumin can bind a wide variety of molecules there are only three sets of binding sites selected by evolution for the transport of (i) nutrients (i.e. fatty acids), (ii) waste (i.e., bilirubin), and (iii) precursor of neurotransmitters (i.e., L-TRP).

It has been shown, for example, in Soltys, B. and Hsia, J. C. (1978) J. Biol. Chem. 253: 3029, that the binding of a molecule to one site can allosterically modulate the binding of a second molecule to a distant site as a result of conformational change of the albumin molecule. Thus, it is important to understand the binding specificity and mechanism of albumin so that the availability of nutrients, hormones and drugs can be modulated to regulate restorative processes, for example, onset and quality of sleep, in man.

It is known, for example, from Gessa, G. L. and Tagliamonte, A. (1974) In: Aromatic amino acids in the brain, Elsevier Publ., Amersterdam, 1974, that L-tryptophan is the precursor of serotonin and its increase in plasma concentration will enhance brain L-TRP levels and presumably brain serotonin levels as well. Serotonin is a neurotransmitter and is involved in a number of physiological processes including influence on sleep. For example, it has been shown in Hartmann, E. (1972) J. Pharm. Pharmacol. 24: 252 that administration of L-TRP reduces latency to sleep, and in Hill, S. Y. and Reyes, R. B. (1978) Psychopharmacol. 58: 229 to induce REM latency in rats.

Because of high albumin concentrations in plasma, the majority of L-TRP is albumin-bound under physiological conditions. It is thus postulated that displacement of L-TRP from albumin will raise the free plasma level of L-TRP and brain serotonin levels which consequently influence the onset or quality of sleep.

It is thus an object of the invention to inhibit the binding of L-TRP to serum albumin by providing a modulator which competes with L-TRP for the same binding site on serum albumin, the modulator having a higher affinity than L-TRP for albumin.

BRIEF DESCRIPTION OF THE INVENTION

According to the invention, a method of inhibiting L-tryptophan to serum albumin binding in a biological fluid, such as blood, containing L-tryptophan and serum albumin, is provided comprising adding to the fluid cis-parinaric acid in a molar ratio to serum albumin of about 0.5:1.0 to 4.0:1.

Cis-parinaric acid is a naturally occurring fatty acid also known under the names cis, trans, trans, cis-9,11,13,15-octadecatetraenoic acid, α-parinaric acid and cis-parinarate. The molecular formula is $C_{18}H_{28}O_2$.

BRIEF DESCRIPTION OF THE DRAWING

In the drawings which seem to illustrate the embodiments of the invention,

FIGS. 1-4 are graphs which illustrate the binding effects of various ligands on the binding of L-TRP to serum albumin.

DETAILED DESCRIPTION OF THE INVENTION

The inhibitory effect of cis-parinaric acid on L-tryptophan (L-TRP) binding to human serum albumin was compared to that of sterate and bilirubin by an equilibrium dialysis technique. The primary L-TRP, bilirubin and stearate binding sites were shown to be independent. However, both the secondary binding sites of stearate (2nd to 4th mole) and bilirubin (2nd and 3rd mole) appear to overlap with the L-TRP binding site. Of the three, cis-parinaric acid is the most effective in inhibiting the L-TRP binding to albumin as compared to stearate and bilirubin. Two moles of cis-parinaric acid reduces the affinity (Ka) of L-TRP for albumin by 80% compared to 20% to that of stearate. This difference suggests that the L-TRP binding site may be the primary cis-parinaric acid site(s) on human serum albumin. The binding site-site relationship of these ligands can be accommodated by an allosteric domain model of three sets of dianionic ligand binding sites with distinct specificity on albumin.

Materials and Methods

Human serum albumin (Fraction V) was purchased from Sigma, St. Louis, MO. The protein was defatted with activated charcoal according to Chen, R. F. (1967), J. Biol. Chem 242: 173-181 and monomeric albumin purified as previously described in Soltys, B. J. and Hsia, J. C. (1977), J. Biol. Chem. 252: 4043-4048. Protein concentration was determined by absorption of ultraviolet light, assuming $E_{279\ nm}^{1\%} = 5.30$ according to Clark, P., Rachinsky, M. R. and Foster, J. F. (1962), J. Biol. Chem. 237: 2509-2513. The sodium salt of cis-parinaric acid was dissolved in $1 \times 10^{-4}$ M albumin in Ringer's buffer. The Ringer's buffer contained 110 mM NaCl, 5 mM KCl, 1.2 mM $MgSO_4$, 1.2 mM $KH_2PO_4$ and 10 mM $Na_2HPO_4$ at a pH of 7.4 at 37° C. L-tryptophan, stearate and bilirubin were also purchased from Sigma, St. Louis, MO. cis-parinaric acid was purchased from Molecular Probes Inc., Plano, TX. L-[side chain-3-$^{14}$C]-tryptophan ($^{14}$C-L-TRP) was purchased from New England Nuclear, Boston, Mass. Fatty acids and bilirubin were dissolved in albumin solution essentially as previously described in Soltys, B. J. and Hsia, J. C. (1977), J. Viol. Chem. 252: 4043-4048. Briefly, fatty acid or bilirubin (sodium salt) in methanol was dried under vacuum in dim light to form a thin film in a small glass vial. The albumin solution was added to the vial and gently blended on a Vortex mixer until optically clear.

Equilibrium dialysis cells (approximately 200 μl total capacity) with injection/sampling ports were used. Dialysis membranes (Canlab, Toronto, Ont), previously boiled in distilled water, were placed on one half-cell and then the two half-cells were bolted together. 100 ul of albumin ($1 \times 10^{-4}$ M), or its ligand complex was added to one side of the dialysis cells, while 100 μl of a solution of $^{14}$C-L-TRP was added to the other side.

The cells were sealed with tape and incubated with slight oscillation at 37±0.5° C. in a jacketed incubator (Model 3314, Forma Scientific, Marietta, OH). The cells contained total amount of L-TRP varying from 0.5 to 20 times the number of moles of albumin. After six hours incubation, 25 μl samples were drawn from the albumin side and the buffer side of each cell. These were counted in 6 ml plastic scintillation vials (Canlab) containing 5 ml Aquasol (New England Nuclear) in a liquid scintillation counter (LS 9000, Beckman, Irvine, CA). A quench curve was constructed to correct for quenching of counts by bilirubin.

RESULTS AND DISCUSSION

Effect of cis-Parinaric acid on L-TRP Binding Capacity of Albumin

The binding of L-TRP to human serum albumin in the presence of cis-parinaric acid at molar ratios to albumin of 0, 0.5, 1.0, 2.0, 3.0 and 4.0 is illustrated in FIG. 1 in the form of Scatchard plots, (i.e., as the variation of r/c against r, where r equals the number of moles of L-TRP bound per mole of albumin, and c is the concentration of free (dializable) L-TRP). The equation for the Scatchard plot is $$r/c = nKa - rKa$$

where n is the number of binding sites and Ka is the apparent association constant. Thus the r-intercept is n and the r/c-intercept is nK (a measure of binding capacity), while the negative slope yields the Ka.

L-TRP has been shown in McMenamy, R. H. and Onaley, J. L. (1958), J. Biol. Chem. 233: 1436-1447, to have one primary binding site on human serum albumin and this was confirmed in the present study (FIG. 1). However, in the presence of 4.0 moles of cis-parinaric acid, the Scatchard plot of L-TRP binding to albumin is in the form of a horizontal line. This indicates that the primary binding site of L-TRP is completely blocked and what remains is the non-specific binding. At a lower molar ratio (0.5 to 1.0) of cis-parinaric acid, a 25 and 50% reduction of albumin binding capacity for L-TRP was observed (FIG. 1). The remaining L-TRP binding capacity of albumin was abolished upon the addition of the second and third molar equivalent of the fatty acid.

Effect of Stearate on L-TRP Binding Capacity of Albumin

FIG. 2 shows the Scatchard plots of the isotherm of the L-TRP binding to albumin in the presence of 0.5, 1.0, 2.0, 3.0 and 4.0 molar equivalents of stearate. Contrary to the effect of cis-parinaric acid, low molar ratio (0.5 to 1.0) of stearate has little effect (total reduction of approximately 15%) on the albumin binding capacity of L-TRP. However, at higher molar ratios (2.0 to 4.0) the inhibitory effect of stearate is similar to the equivalents of cis-parinaric acid. The specific L-TRP binding capacity of albumin is completely abolished in the presence of 4 moles of cis-parinaric acid while residue binding capacity remains in the presence of stearate.

Effect of Bilirubin on L-TRP Binding Capacity of Albumin

FIG. 3 shows the Scatchard plots of L-TRP binding to albumin in the presence of 0, 1.0, 2.0 and 3.0 molar equivalents of bilirubin. Consistent with the results of Jacobsen and Jacobsen, in Jacobsen, C. and Jacobsen, J. (1979), Biochem. J. 181: 251-253, the presence of one molar equivalent of bilirubin did not affect the L-TRP binding to albumin. However, progressive inhibition of the binding capacity was observed in the presence of the second and third molar equivalents of bilirubin.

The specificity of the fatty acids and bilirubin in reducing the albumin binding capacity for L-TRP is summarized in FIG. 4.

These results show that (i) one mole of bilirubin and stearate have little effect on L-TRP binding while cis-parinaric acid has a strong inhibitory effect, and (ii) at higher molar ratios, all three ligands inhibit L-TRP binding, with cis-parinaric acid being the most effective. These results further suggest that the L-TRP binding site may be the primary cis-parinaric acid site on albumin.

Intake of cis-parinarate in Presence of L-TRP

Applicant has discovered that a naturally occurring long chain fatty acid (i.e., cis-parinarate) has specific affinity to the primary tryptophan binding site on serum albumin. We have shown it to displace up to 90% of albumin-bound tryptophan at a 2:1 cis-parinarate-to-albumin ratio. It is noteworthy that free fatty acid to albumin ratio varies normally between approximately 0.5 and 4.0. Thus simultaneous intake of an "enhancer", i.e., cis-parinarate, and L-tryptophan will lead to increased availability of tryptophan for serotonin synthesis. It is proposed that the use of such an "enhancer" may lead to more uniformity and utility of the soporiforic effect of tryptophan in man.

In "Short Term Repetitive Administration of Oral Tryptophan in Normal Man-Effects on Blood-tryptophan Serotonin Kynurenine Concentrations" by Arthur Yuwiler et al - Archives Gen-Psychiatry, Vol. 38, pp. 619-626, June 1981, it is shown that dosages of tryptophan of the order of 50-100 mg. per Kg of body weight may be usefully administered to man.

Thus, applicant contemplates an enhanced soporiforic composition for oral administration to man comprising 50-100 mg/kg body weight and cis-parinaric acid in a molar ratio to serum albumin in the blood of about 0.5:1 to 4.0:1.

The embodiments of the invention in which an exclusive property or privilege is claimed are defined as follows:

1. A method of inhibiting L-tryptophan to serum albumin binding in blood or a blood fraction fluid containing L-tryptophan and serum albumin, comprising adding to the fluid cis-parinaric acid in a molar ratio to serum albumin of about 0.5:1 to 4.0:1.

2. A method according to claim 1 wherein cis-parinaric acid is added to the fluid in a molar ratio to serum albumin of 1:1.

3. A method according to claim 1 wherein cis-parinaric acid is added to the fluid in a molar ratio to serum albumin of 3:1.

4. A method according to claim 1, 2 or 3, wherein the cis-parinaric acid is added to the fluid in the form of a pharmaceutically acceptable acid addition salt in Ringer's buffer at pH of about 7.4.

5. A method according according to claim 1, 2 or 3, wherein the cis-parinaric acid is added to the fluid in the form of the sodium salt in Ringer's buffer at a pH of about 7.4.

6. A method according to claim 1 wherein cis-parinaric acid is added to the fluid in a molar ratio to serum albumin of 0.5:1.

7. A method according to claim 1 wherein cis-parinaric acid is added to the fluid in a molar ratio to serum albumin of 2:1.

8. A method according to claim 1 wherein cis-parinaric acid is added to the fluid in a molar ratio to serum albumin of 4:1.

9. A method according to claim 6, 7 or 8, wherein the cis-parinaric acid is added to the fluid in the form of a pharmaceutically acceptable acid addition salt in Ringer's buffer at a pH of about 7.4.

10. A method according to claim 6, 7 or 8, wherein the cis-parinaric acid is added to the fluid in the form of the sodium salt in Ringer's buffer at a pH of about 7.4.

11. A soporiforic composition for oral administration to man, comprising cis-parinaric acid together with Ringer's buffer at a pH of about 7.4, the cis-parinaric acid present in said composition in an amount sufficient to provide a molar ratio of from 0.5:1 to 4.0:1 of cis-parinaric acid to serum albumin in the blood when orally administered to man.

* * * * *